(12) United States Patent
Zhang

(10) Patent No.: US 12,148,519 B2
(45) Date of Patent: Nov. 19, 2024

(54) APPARATUSES AND METHODS FOR MODELLING AND CONTROL OF ICE FORMATION DURING CRYOABLATION TREATMENTS

(71) Applicant: Varian Medical Systems, Inc., Palo Alto, CA (US)

(72) Inventor: Hongxuan Zhang, Austin, TX (US)

(73) Assignee: Varian Medical Systems, Inc., Palo Alto, CA (US)

( * ) Notice: Subject to any disclaimer, the term of this patent is extended or adjusted under 35 U.S.C. 154(b) by 237 days.

(21) Appl. No.: 17/664,228

(22) Filed: May 20, 2022

(65) Prior Publication Data

US 2023/0377713 A1  Nov. 23, 2023

(51) Int. Cl.
*G16H 20/40* (2018.01)

(52) U.S. Cl.
CPC .................................. *G16H 20/40* (2018.01)

(58) Field of Classification Search
None
See application file for complete search history.

(56) References Cited

U.S. PATENT DOCUMENTS

| | | |
|---|---|---|
| 2006/0155267 A1 | 7/2006 | Berzak et al. |
| 2010/0168725 A1* | 7/2010 | Babkin ................. A61B 18/02 606/21 |
| 2016/0220190 A1* | 8/2016 | Zhang .................. A61B 5/7253 |
| 2017/0020623 A1* | 1/2017 | Glossop ................ A61B 90/11 |
| 2017/0209218 A1* | 7/2017 | Sahay .................... A61B 6/487 |
| 2020/0345426 A1* | 11/2020 | Glossop ................ A61B 34/10 |
| 2021/0092436 A1* | 3/2021 | Zhang .................... H04N 19/61 |
| 2023/0404642 A1* | 12/2023 | Link, Jr. ............... C07K 14/001 |

FOREIGN PATENT DOCUMENTS

WO    2023225176 A1    11/2023

OTHER PUBLICATIONS

Jun Y. Chan, Ean H. Ooi, Sensitivity of thermophysiological models of cryoablation to the thermal and biophysical properties of tissues, Cryobiology, vol. 73 issue 3, 2016 pp. 304-315: (https://www.sciencedirect.com/science/article/pii/S0011224016303868) (Year: 2016).*
PCT International Search Report and Written Opinion for PCT/US2023/022704 issued Aug. 23, 2023.

* cited by examiner

*Primary Examiner* — Katherine Kolosowski-Gager
(74) *Attorney, Agent, or Firm* — Duane Morris LLP

(57) ABSTRACT

A method of performing a cryoablation treatment includes obtaining an ice formation model and preparing a cryoablation treatment plan based on the ice formation model and one or more characteristics of the target tissue. The method also includes initiating a cryoablation freezing cycle and obtaining ice formation data that describes one or more characteristics of ice being formed during the cryoablation freezing cycle. The method also includes determining a position of one or more isotherms of the ice being formed based on the ice formation data and the ice formation model.

20 Claims, 9 Drawing Sheets

FIG. 4

FIG. 5 ively form ice that freezes healthy tissue or body structures adjacent to or surrounding the target tissue. In addition, traditional and existing systems and methods are poor at determining the location of isotherms or other characteristics of the freezing process. There exists a need, therefore, for improved cryoablation systems and methods to monitor, control and adapt to the particular circumstances of cryoablation treatments and to efficiently and effectively predict and form ice in a period of time and in a desired size, shape and location.

APPARATUSES AND METHODS FOR MODELLING AND CONTROL OF ICE FORMATION DURING CRYOABLATION TREATMENTS

FIELD

The present disclosure relates to apparatuses and methods for the modelling and control of ice formation during cryoablation treatments.

BACKGROUND

This section provides background information related to the present disclosure which is not necessarily prior art.

Systems and methods for providing cryoablation treatments may include cryoablation probes that are introduced at or near target tissue in a patient. A cryoablation system may include an extremely cold cryogen (liquid, gas, or mixed phase) that may be passed through a probe in thermal contact with the target tissue. Heat from the tissue passes from the tissue, through the probe, and into the cryogen that removes heat from the targeted tissue. This removal of heat causes tissue to freeze, resulting in the destruction of the targeted tissue. When the tissue freezes, ice forms typically in an iceball. The iceball may be in the form a sphere, ellipsoid or other shape. It is desirable to perform cryoablation treatments such that the target tissue is completely frozen and that the freezing of surrounding tissues and/or body structures is minimized.

Traditional or existing systems and methods often include predetermined test procedures that are determined experimentally in a laboratory environment. Traditional or existing systems and methods do not include the capability to accurately predict and/or monitor the formation of ice during cryoablation treatments. As such, the ice that forms using existing and traditional methods and systems may not perform as efficiently and effectively as desired. Furthermore, treatments using existing and traditional methods may unnecessarily form ice that freezes healthy tissue or body structures adjacent to or surrounding the target tissue. In addition, traditional and existing systems and methods are poor at determining the location of isotherms or other characteristics of the freezing process. There exists a need, therefore, for improved cryoablation systems and methods to monitor, control and adapt to the particular circumstances of cryoablation treatments and to efficiently and effectively predict and form ice in a period of time and in a desired size, shape and location.

SUMMARY

This section provides a general summary of the disclosure, and is not a comprehensive disclosure of its full scope or all of its features.

In various embodiments of the present disclosure, apparatuses and methods for performing cryoablation treatments are provided. The apparatuses and methods may include improvements directed to determining ice formation models that predict the growth of ice during cryoablation treatments. The ice formation models can be implemented as affine models that predict the growth of ice along various directions from a location on a cryoprobe. The ice formation models can predict a location of one or more isotherms in the iceball that is formed during a freezing cycle of a cryoablation treatment. With this information, the operating conditions of the cryoablation apparatus can be adjusted, if necessary, to grow an iceball having a predetermined size, shape and temperature profile. The location of the isotherms can be positioned as desired to improve the effectiveness of the cryoablation treatment and/or to minimize detrimental effects to healthy tissue that may surround the target tissue.

In some embodiments of the present disclosure, a cryoablation system may include at least one computing device. The at least one computing device may be configured to obtain an ice formation model and prepare a cryoablation treatment plan based on the ice formation model and one or more characteristics of the target tissue. The computing device may be further configured to initiate a cryoablation freezing cycle and to obtain ice formation data that describes one or more characteristics of ice being formed during the cryoablation freezing cycle. The computing device may also determine a position of one or more isotherms of the ice being formed based on the ice formation data and the ice formation model.

In one aspect, the ice formation model may describe growth of ice during a cryoablation freezing cycle in multiple directions from a predetermined position on a cryoablation probe.

In another aspect, the ice formation model may include an affine model configured to predict growth of ice in a plurality of directions from a predetermined position on a cryoablation probe.

In another aspect, the one or more characteristics of the target tissue may include a type of tissue, a size of the tissue, and a shape of the tissue.

In another aspect, the ice formation data may include imaging data obtained from an imaging apparatus.

In another aspect, the imaging data may indicate an outer edge of the ice being formed during the cryoablation cycle.

In another aspect, each isotherm of the one or more isotherms may indicate a boundary at which a predetermined temperature threshold has been reached.

In another aspect, at least one of the one or more isotherms corresponds to a boundary at which the ice has reached −20° C.

In another aspect, the step of determining a position of one or more isotherms may include determining a position relative to the cryoablation probe of a boundary at which ice has reached −20° C. based on a position of an edge surface of the ice and the ice formation model.

In another aspect, the computing device may be further configured to compare the ice formation data to the ice formation model to determine whether the ice being formed during the cryoablation treatment is growing in a predicted manner using one or more affine ratios and adjust growth of the ice being formed when the ice formation data indicates that the one or more affine ratios are greater than a predetermined upper threshold or less than a predetermined lower threshold.

In some embodiments of the present disclosure, a method of performing a cryoablation treatment may include obtaining an ice formation model and preparing a cryoablation treatment plan based on the ice formation model and one or more characteristics of the target tissue. The method may also include initiating a cryoablation freezing cycle and obtaining ice formation data that describes one or more characteristics of ice being formed during the cryoablation freezing cycle. The method may also include determining a position of one or more isotherms of the ice being formed based on the ice formation data and the ice formation model.

In one aspect, the ice formation model may describe growth of ice during a cryoablation freezing cycle in multiple directions from a predetermined position on a cryoablation probe.

In another aspect, the ice formation model may include an affine model configured to predict growth of ice in a plurality of directions from a predetermined position on a cryoablation probe.

In another aspect, the one or more characteristics of the target tissue may include a type of tissue, a size of the tissue, and a shape of the tissue.

In another aspect, the ice formation data may include imaging data obtained from an imaging apparatus.

In another aspect, the imaging data may indicate an outer edge of the ice being formed during the cryoablation cycle.

In another aspect, each isotherm of the one or more isotherms may indicate a boundary at which a predetermined temperature threshold has been reached.

In another aspect, at least one of the one or more isotherms corresponds to a boundary at which the ice has reached −20° C.

In another aspect, the step of determining a position of one or more isotherms may include determining a position relative to the cryoablation probe of a boundary at which ice has reached −20° C. based on a position of an edge surface of the ice and the ice formation model.

In another aspect, the computing device may be further configured to compare the ice formation data to the ice formation model to determine whether the ice being formed during the cryoablation treatment is growing in a predicted manner using one or more affine ratios and adjust growth of the ice being formed when the ice formation data indicates that the one or more affine ratios are greater than a predetermined upper threshold or less than a predetermined lower threshold.

In some embodiments of the present disclosure, a method of creating a model for predicting ice formation during a cryoablation treatment is provided. A method of creating a model for predicting ice formation during a cryoablation treatment may include measuring ice growth at a plurality of time intervals wherein the ice growth is measured in a plurality of directions from a predetermined location on a cryoablation probe and determining relationships between operating conditions of the cryoablation probe and the ice growth for each direction of the plurality of directions from the predetermined location on the cryoablation probe.

In one aspect, the plurality of directions are linear directions from a common location on the cryoablation probe.

In another aspect, the step of determining relationships may include determining one or more affine ratios at each of the plurality of time intervals for each of the plurality of directions.

In some embodiments of the present disclosure, a method for creating a treatment plan for use during a cryoablation treatment is provided. The method may include obtaining patient data comprising information regarding a location of a target tissue in a patient and obtaining an ice formation model that describes growth of ice in a plurality of directions from a predetermined location on a cryoablation probe. The method may also include determining operating parameters for a cryoablation system based on the patient data and the ice formation model wherein the cryoablation system is configured to provide a cryogen to the cryoablation probe.

In another aspect, the method may also include determining a duration and location of a final iceball size.

In another aspect, the method may also include determining a target profile for one or more affine ratios based on the ice formation model.

In another aspect, the target profile may describe a target value for the one or more affine ratios during a plurality of time intervals in the cryoablation treatment.

In another aspect, the method may also include predicting a position of one or more isotherms in a final ice formation.

In another aspect, each isotherm of the one or more isotherms may indicate a boundary at which a predetermined temperature threshold has been reached.

In another aspect, at least one of the one or more isotherms corresponds to a boundary at which the final ice formation has reached −20° C.

In another aspect, the step of predicting a position of one or more isotherms may include determining a position relative to the cryoablation probe of a boundary at which ice has reached −20° C. based on the ice formation model.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is a diagram illustrating an example output of an iceball growing model at a first period of time.

FIG. 5 is a diagram illustrating an example output of the iceball growing model of FIG. 4 at a second period time.

Corresponding reference numerals indicate corresponding parts throughout the several views of the drawings.

DETAILED DESCRIPTION

Figure 1:
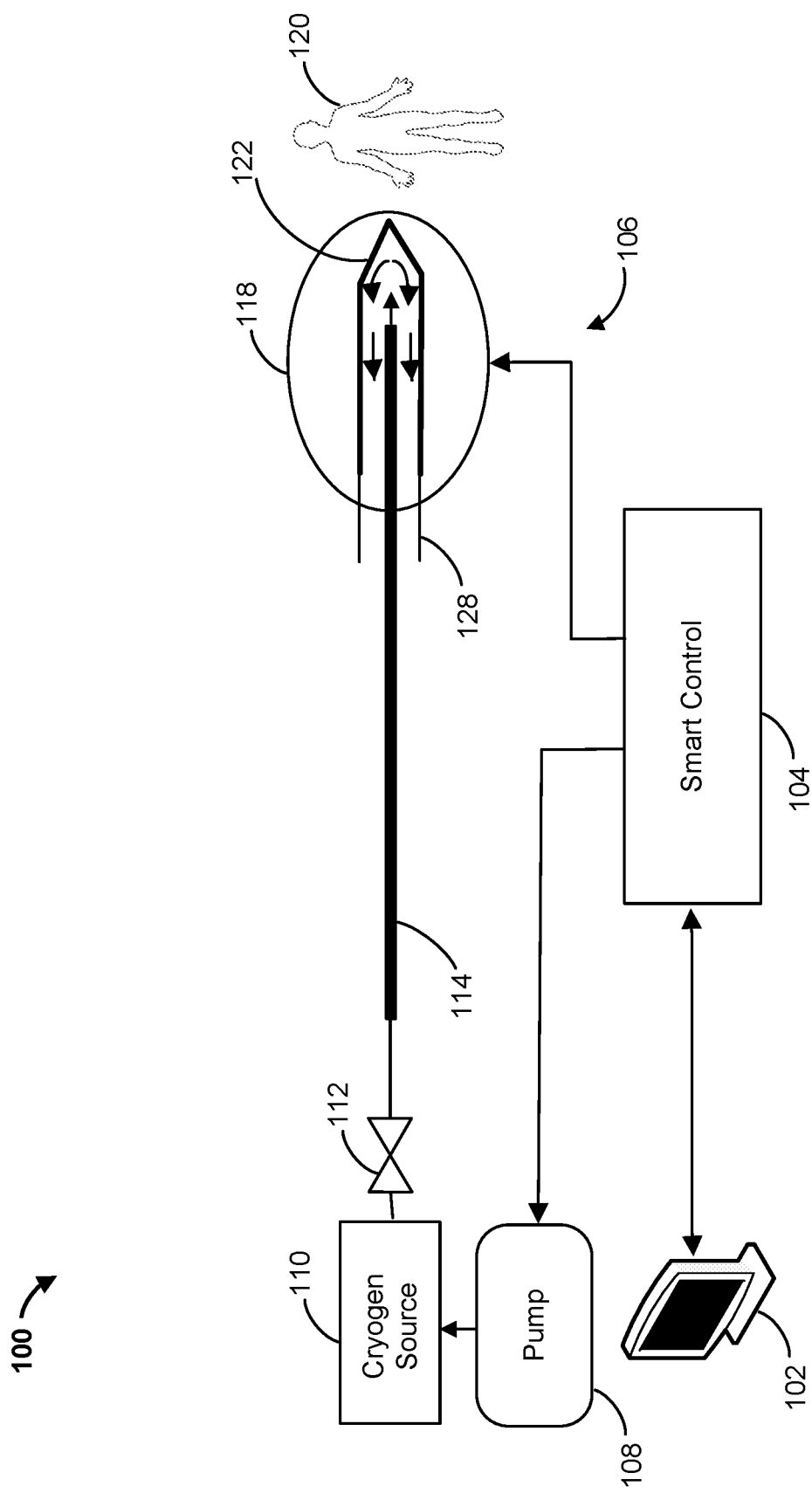
FIG. 1 is a diagram illustrating an example cryoablation system in accordance with some embodiments of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In some embodiments of the present disclosure, methods are provided that allow the performance of cryoablation treatments using an ice formation model. The ice formation models of the present disclosure can be used to prepare a cryoablation treatment plan that may describe the operating conditions to be used during a cryoablation treatment. The ice formation models of the present disclosure may be used, for example, to predict the growth, size and shape of ice that is formed during a cryoablation treatment. The methods of the present disclosure may utilize one or more ice formation models so that target tissue (e.g., tumor or other abnormal tissue) can be destroyed during the freezing cycle of the cryoablation treatment.

The methods of the present disclosure may be used in connection with a cryoablation apparatus in which a cryoablation probe may be inserted into a patient at or near the target tissue. When a suitable cryogen is passed to the probe, heat can be removed from the region proximate the cryoablation probe. Ice typically begins to form when sufficient heat is removed lowering the temperature of the target tissue and the region surrounding the cryoablation probe. It is desirable to lower the temperature to a sufficient threshold or to a freezing temperature range so that the ice forms quickly so that the cryoablation treatment and/or the freezing cycle of the treatment is limited. In some instances, it is desired to limit the freezing cycle to less than 10 minutes. In other examples, the duration of the freezing cycle can be based on a particular temperature. In many clinical settings, it can be desirable to lower the temperature and freeze the target tissue to at least −20° C. for at least three minutes. When such a temperature and duration is achieved there is a significant likelihood that that the target tissue has been destroyed. In some example cryoablation treatments, the treatment may include multiple freezing cycles that may be performed between thawing cycles.

As can be appreciated, it is desirable to ensure that the entire target tissue (e.g., an entire tumor) is destroyed during the cryoablation treatment. To increase the likelihood that this occurs, it is desirable to understand the temperatures and size of the ice that is being formed during the cryoablation treatment. It can be difficult to acquire this information in a clinical setting, however, because existing equipment and cryoablation apparatuses are limited in the amount and type of information that can be supplied in real time to a medical professional. For example, imaging systems may be used in connection with a cryoablation treatment. Such imaging systems may include, for example, ultrasound device, CT scan devices, x-ray devices and/or MRI devices. Such imaging processes, however, are poor at delivering real-time and/or accurate information regarding ice formation during treatment. Traditional and existing imaging devices typically can only provide information or indications of overall size of the ice or iceball that is formed during a cryoablation treatment. Imaging systems do not provide temperature information.

Furthermore, it is desirable to minimize the impact of the cryoablation treatment on the patient and to minimize damage and/or disruption to healthy tissue. Thus, it is desirable to minimize the size of the cryoablation probe and to limit the number of additional measurement devices that are used during the cryoablation treatment.

In light of the foregoing, traditional and existing cryoablation methods and systems are poor at indicating a location of the −20° C. temperature boundary (or isotherm) that may be located in the ice or iceball during the cryoablation treatment. The location of such boundary, however, is important in determining the effectiveness of the cryoablation treatment. In existing or traditional methods, an imaging system may be used to determine a size, shape or location of the iceball but such images may only indicate the outer profile (or overall size and shape) of the iceball but the temperature of the ice and the temperature profile of the internal regions of the iceball are unknown.

The systems and methods of the present disclosure are improvements over traditional and existing systems by incorporating the use of ice formation models that can predict the growth rate and other characteristics of the ice that is formed during a cryoablation treatment. The use of the ice formation models of the present disclosure may allow a location of the −20° C. temperature boundary or other isotherms of the ice formation to be determined. The use of the methods and systems of the present disclosure improve the likelihood that the target tissue is destroyed during a cryoablation treatment. In addition, the duration and impact of the cryoablation treatment on healthy tissue of the patient can be minimized. Still further the size, shape and growth rate of the ice that is formed during the cryoablation treatment can be adjusted and/or implemented to correspond to the size, shape and location of the target tissue more accurately than when using traditional or existing methods.

In some examples of the present disclosure, the ice formation models can be affine models. In such examples, the models can predict a growth of ice in a plurality of directions from a predetermined location on the cryoablation probe. One or more affine ratios can be used to measure, predict or otherwise characterize the ice growth in the affine ice formation models.

Referring now to FIG. 1, an example cryoablation system 100 is shown. The cryoablation system 100 may include a cryoablation computing device 102, a smart control 104, a pump 108, a cryogen source 110, an inlet valve 112, a cryogen supply 114, and a cryoprobe 128. The pump 108, the cryogen source 110, the inlet valve 112, the cryogen supply 114, and the cryoprobe 128 may operate to deliver a cryogen from the cryogen source 110 to the cryoprobe 128 to perform a cryoablation treatment. The cryogen (e.g., liquid nitrogen) can be stored in the cryogen source 110, such as a dewar or other suitable container, and then delivered to the cryoprobe 128 via the cryogen supply 114. The cryogen may expand at a tip 122 of the cryoprobe 128 and cool the tip 122 of the cryoprobe 128 to a temperature at which the target tissue of a patient 120 begins to freeze forming an iceball 118.

The term iceball may be used in the present disclosure to describe various types of ice formations that may occur as a result of the cryoablation freezing cycle. While the term iceball may be used, it should be understood that the ice that is formed during the cryoablation treatment may have shapes other than a ball or sphere shape. The iceball may be elliptical, or have other shapes that may be formed due to ice growth at different rates and to different extents in various directions from the cryoprobe 128.

The cryoprobe 128 can be positioned at or near a target tissue (e.g., a tumor) in the patient 120. In this manner, the target tissue can be frozen destroying the target tissue. One or more freezing cycles can be performed in order to destroy the target tissue. The iceball 118 may form at the target tissue in the patient 120 during the freezing cycle. It is desirable to control and form the iceball 118 in a predetermined manner so the iceball 118 forms to a desired size, shape and rate so that the target tissue is frozen in the iceball 118 for a desired period of time. It is also desirable to form the iceball 118 with the desired size, shape and rate so that healthy tissue or body structures near the target tissue are not harmed by the freezing cycle. It can be desirable, for example, to limit a size of the iceball 118 so that it does not form and freeze healthy tissue.

A treatment plan can be determined prior to the performance of the cryoablation treatment. The treatment plan can detail and/or describe the various steps of the process and various aspects of the treatment such as the types of equipment to be used, a positioning of the cryoprobe, temperatures of the cryoprobe, duration of freezing (and thaw cycles) as well as a quantity of cycles. The treatment plan may also include a size, location, shape, growth rate and duration of an iceball. The treatment plan may be determined by a medical professional and/or by others. As will be further described, the treatment plan can be determined using one or more of the ice formation models created using methods of the present disclosure.

In some examples, the cryoablation computing device 102 may determine or recommend a treatment plan after health, patient, and other information is input into the cryoablation computing device 102 or such information is retrieved or otherwise obtained by the cryoablation computing device 102. The cryoablation computing device 102 may any suitable computing device such as a workstation, computer, laptop, tablet, server or the like.

As further shown, the cryoablation system 100 includes the smart control 104 that may be coupled to the cryoablation computing device 102, to the cryoprobe 128, and to the pump 108. The smart control 104 may be any suitable controller, PLC, data acquisition unit, control unit or the like that can perform the operations described herein. In some examples, the cryoablation computing device 102 and the smart control 104 can be combined in a single device. In others, they may be separate devices as shown. The smart control 104 may operate to obtain ice formation measurement information from measurement points. The measurement points may include suitable sensors, measurement locations, or the like that can obtain ice formation measurement information from locations on or near the tip 122 of the cryoprobe 128. The ice formation measurement information may provide temperature information at predetermined locations in order to provide information regarding the growth of the ice at the target tissue. The measurement points may include temperature sensors, thermocouples, thermistors, impedance sensors, and the like. Such measurement points may be incorporated into the cryoprobe 128 and/or into a separate measurement lead.

The smart control 104 may operate to obtain the ice formation measurement information and provide the information to the cryoablation computing device 102. While not shown, the smart control 104 and/or the cryoablation computing device 102 may also be coupled to an imaging device such as an x-ray apparatus, an ultrasound apparatus, a CT scan apparatus, an MRI apparatus or the like. The imaging information from such devices may be used during a treatment, before the treatment and/or after the treatment to provide information regarding ice formation and/or information regarding the target tissue and other tissues of the patient 120. The cryoablation computing device 102 may then perform various operations to determine characteristics of the ice being formed during a cryoablation treatment. The cryoablation computing device 102 may, for example, use the imaging information and one or more ice formation models to determine and/or predict characteristics of the iceball such as the location of isotherms or other temperature information.

After determining characteristics of the ice, the cryoablation computing device 102 may take action to adjust, change, modify or otherwise control the one or more operating parameters of the cryoablation system 100. In some examples, the cryoablation computing device 102 may adjust the flow of the cryogen provided from the cryogen source 110 to the cryoprobe 128. The cryoablation computing device 102 may be coupled to the pump 108. The pump 108 can be an adjustable, programmable, or otherwise controllable pump. The pump 108 may allow for the flow rate, flow volume, flow speed, pressure or other characteristic of the flow of cryogen to be modified, controlled or customized. In some examples, the pump 108 can operate to deliver the cryogen to the cryoprobe 128 in a pulsed manner using pulse width modulation (PWM). In such examples, the pump 108 can be controlled to deliver a flow of cryogen at a desired frequency, pulse width, pulse amplitude or other desired flow characteristic.

While not shown, the smart control 104 and/or the cryoablation computing device 102 may also be coupled to other information sources. The smart control 104 and/or the cryoablation computing device 102 may be coupled to a medical information database or other health status information sources that may include information regarding the patient 120 and/or to other clinical treatment procedures and the like. In some examples, the cryoablation computing device 102 can be coupled to a suitable database or information source, such as a server, that can store one or more ice formation models.

Figure 2:
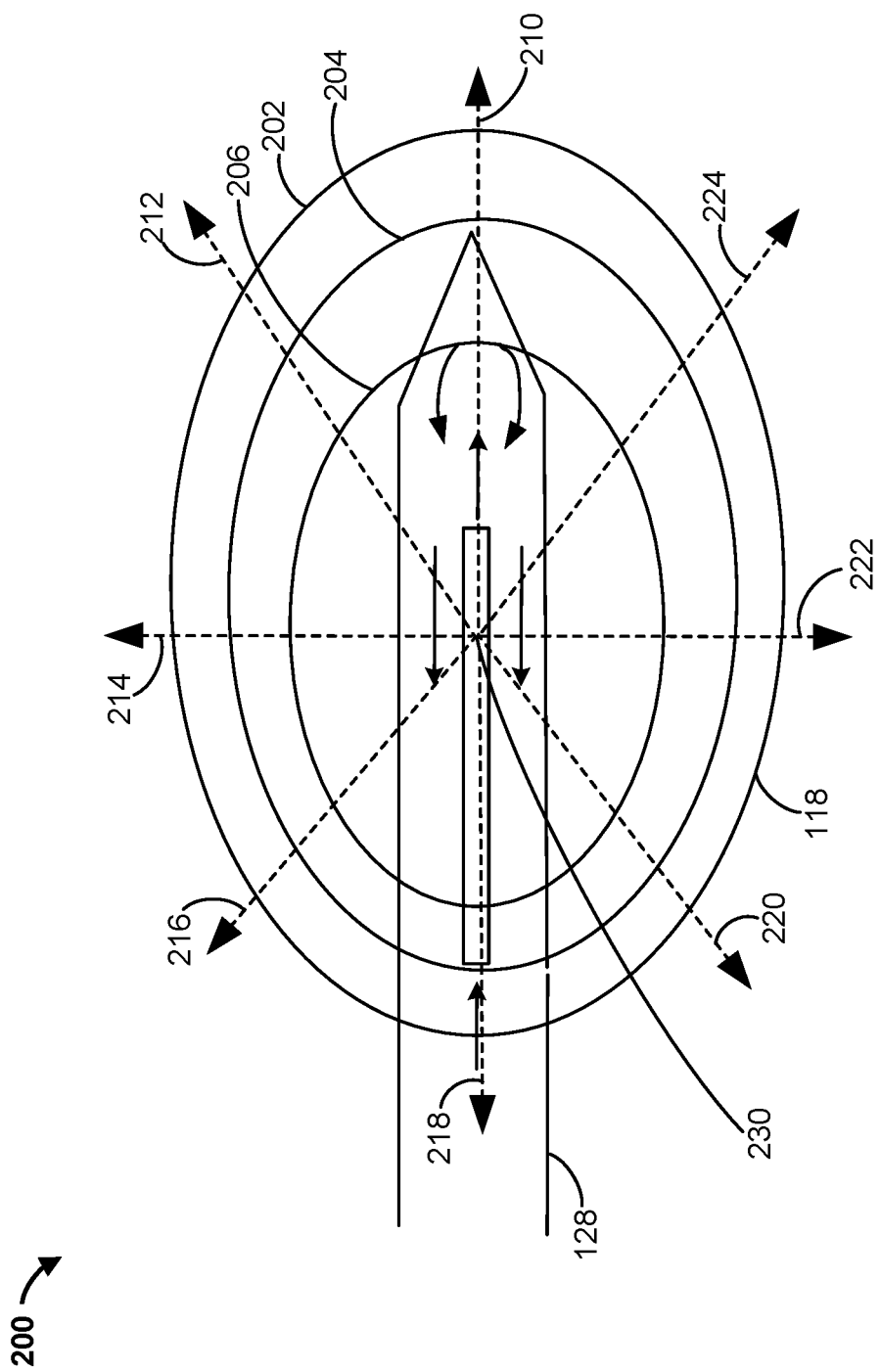
FIG. 2 is an illustration showing an example cryoprobe and an example iceball formed during a cryoablation treatment with various aspects of an example method of modeling a growth of the iceball.

FIG. 2 illustrates an example iceball 118 and a cryoprobe 128. The iceball 118 may be formed during a cryoablation procedure. The iceball 118 can be characterized by one or more isotherms. In this example, the iceball 118 is shown with a first isotherm 202, a second isotherm 204, and a third isotherm 206. The isotherms 202, 204, and 206 define boundaries at which a predetermined temperature has been achieved. In the example shown, the first isotherm 202 may define a 0° C. isotherm. The first isotherm 202 defines the outer edge of the iceball 118 and defines a boundary of the iceball at which all locations inside of the first isotherm 202 have achieved a temperature of 0° C. or lower. As can be appreciated, the internal regions of the iceball 118 may have a temperature lower than 0° C.

The second isotherm 204 may define a lower temperature than the first isotherm 202. In the example shown, the second isotherm 204 may define a boundary of the −20° C. isotherm. Regions of the iceball 118 that are located inside the second boundary may have achieved a temperature of −20° C. or lower. The third isotherm 206 may define still a lower temperature than both the first isotherm 202 and the second isotherm 204. The third isotherm 206 may define a boundary of the −40° C. isotherm. Regions of the iceball 118 that are located inside the third boundary 206 may have achieved a temperature of −40° C. or lower.

It can be important to understand the location and size of the first isotherm 202, the second isotherm 204 and/or the third isotherm 206 during the performance of cryoablation treatments. It is understood that subjecting some tissues to a temperature of −20° C. reliably destroys the tissue. Other tissues are not destroyed unless subjected to lower temperatures of −40° C. In many cryoablation treatments, it is desirable to subject abnormal tissues such as tumors, cancers and the like to a temperature of at least −40° C. in order to reliably destroy the tissue. It is important to understand the location of the −40° C. isotherm so as to fully encapsulate the target tissue (e.g., tumor) within this boundary to destroy the target tissue. It is also desirable to minimize the tissue that is located in the −20° C. isotherm so that damage to healthy tissue is minimized.

In the example shown, the first isotherm 202, the second isotherm 204, and the third isotherm 206 correspond to the 0° C. isotherm, the −20° C. isotherm, and the −40° C. isotherm, respectively. It should be appreciated, however, that the apparatuses and methods of the present disclosure can applied to determine models for determining the location of isotherms having different characteristics or other temperature values.

In one example, an ice formation model can be constructed as an affine model. In such a model, the growth of ice is predicted along one or more directions from a predetermined location on the cryoprobe 128. As shown, the model may include multiple directions from a predetermine location 230 on the cryoprobe. The predetermined location 230 can be any suitable location on the cryoprobe and may be a location of an approximate center of the iceball 118. Multiple directions may extend from the predetermined location 230. In the example shown, the directions are extended as linear paths along which the growth of ice can be measured and modeled.

While any number of directions can be used, the ice formation model may include eight directions in two orthogonal planes. The illustration of FIG. 2 shows eight directions (as will be further explained) in a first plane. As can be appreciated, a similar arrangement of directions or vectors from the predetermined point 230 can also be used. Such additional directions or vectors can be positioned in a plane that is located orthogonal to the plane shown in FIG. 2. Such orthogonal plane can include the predetermined point 230. With at least two orthogonal planes, the ice formation model can model growth of ice in three dimensions. For the sake of brevity, the ice formation model is described with respect to the plane shown in FIG. 2. In other examples, other planes and other quantities of directions or vectors can also be used.

The ice formation model may include eight directions. The eight directions may include a first direction 210, a second direction 212, a third direction 214, a fourth direction 216, a fifth direction 218, a sixth direction 220, a seventh direction 222, and an eighth direction 224. Each direction is directed from the predetermined point 230 and extends linearly at a predetermined angle. The directions may be evenly spaced from one another. In the example shown, the directions are positioned at approximately 45 degrees from one another.

The affine ice formation model can be constructed to predict a growth of ice along each of the eight directions as a function of time. A temperature at any position along each of the directions can also be constructed as part of the model. When the model is constructed, it can be used to determine a location of the first isotherm 202, the second isotherm 204, and the third isotherm 206 at a particular time. For example, the model can predict a location of the first isotherm 202, the second isotherm 204, and the third isotherm 206 as a function of time and of the operating conditions of the cryoablation system. The operating conditions of the cryoablation system can include an operating pressure, flow rate, flow pulse, cryogen temperature, and the like. With the model, the operating conditions of the cryoablation system can be used to adjust and/or change the growth rate, size, location of isotherms or other characteristics of the iceball 118.

The affine ice formation model may be built using experimental data in one example. A test rig can be configured in which a grid or web of temperature sensors can be positioned in an array around a cryoprobe and test tissue. A freezing cycle can be initiated and the temperature at predetermined locations around the cryoprobe can be measured over time. The growth rate of the iceball in the various directions of the affine model can be measured. Such a process can be performed multiple times, at various operating conditions and/or in various tissues and environments. This information can be used to build a correlation between the operating conditions, the tissue and the formation of ice including the location of the isotherms. Regression models can also be used to construct the ice formation model.

In still other examples, machine learning or artificial intelligence can be used. The experimental data can be used to train a machine learning ice formation model using suitable neural networks. Such a trained model can learn the complex relationships between the operating conditions of the cryogen, the tissue and body structures of the patient and the formation of ice and the location of the isotherms. The machine learning model can be adapted to be re-trained using clinical data from cryoablation treatments in addition to the experimental data.

One or affine parameters of affine ratios may be used to build the ice formation model and/or to monitor the growth of ice during a cryoablation treatment. One example ratio is an iceball size growing affine ratio. The iceball size growing affine ratio is characterized by Equation (1) below.

$$\text{Affine\_growing}_i(T_j) = \left| \frac{L_i(T_j)}{L_i(T_{j-1})} \right| \quad \text{Eq. (1)}$$

where Li is a length or distance along one of the i directions from the predetermined point 230 to the outer edge 202 of the iceball 118 at a time Tj measured from the initiation of the freezing cycle. The iceball size growing affine ratio provides a characterization of the growth rate of the iceball.

Another affine ratio that can be used is an iceball size symmetric growing affine ratio that is characterized by Equation (2) below.

$$\text{Affine\_symmetric}_{ij}(T_n) = \left| \frac{L_i(T_n)}{L_j(T_n)} \right| \quad \text{Eq. (2)}$$

where Li or Lj is a length or distance from the predetermined point 230 to the edge of the iceball measured along the direction i or direction j. The lengths are compared in this ratio at the same time Tn.

Another affine ratio that can be used is an iceball thermal freezing energy affine ratio that is characterized by Equation (3) below.

$$\text{Affine\_energy}_{ij} = \left| \frac{\sum_{n=1}^{N} L_i(T_n)^2}{\sum_{n=1}^{N} L_j(T_n)^2} \right| \quad \text{Eq. (3)}$$

where Li or Lj is a length or distance from the predetermined point 230 to the edge of the iceball measured along the direction i or direction j. The lengths are compared in this ratio at the same time Tn. This ratio, however, sums the lengths for each measured time 1 to N.

Another ratio that can be used is an iceball affine symmetric morphology ratio that is characterized by Equation (4) below.

$$\text{Affine\_symmetric} = \sqrt{\sum_{T1}^{T_N} \left( \frac{L_i(T_n)}{L_j(T_n)} \right)^2} \quad \text{Eq. (4)}$$

where the variables used are the same as those noted above. This ratio provides an indication of overall symmetry during the time from 1 to N.

Still another ratio that can be used is an iceball affine shape morphology ratio that is characterized by Equation (5) below.

$$\text{Affine\_shape} = \sqrt{\sum_{i,j=2}^{M_{\text{affine\_direction}}} \sum_{T1}^{T_N} \left( \frac{L_i(T_n)/L_{i-1}(T_n)}{L_j(T_n)/L_{j-1}(T_n)} \right)^2} \quad \text{Eq. (5)}$$

where the variables used are the same as noted above but the ratio includes a summation for each direction i, j to M.

The ratios as described above can each be used as inputs to the model to train or construct the ice formation model. In some examples, the model can be constructed to include algorithms, rules or other features that can be obtained from observing or determining one or more of the ratios. In addition, the ratios can be calculated during the performance of a cryoablation treatment and compared to predicted or predetermined target profiles for the ratios.

Figure 3:
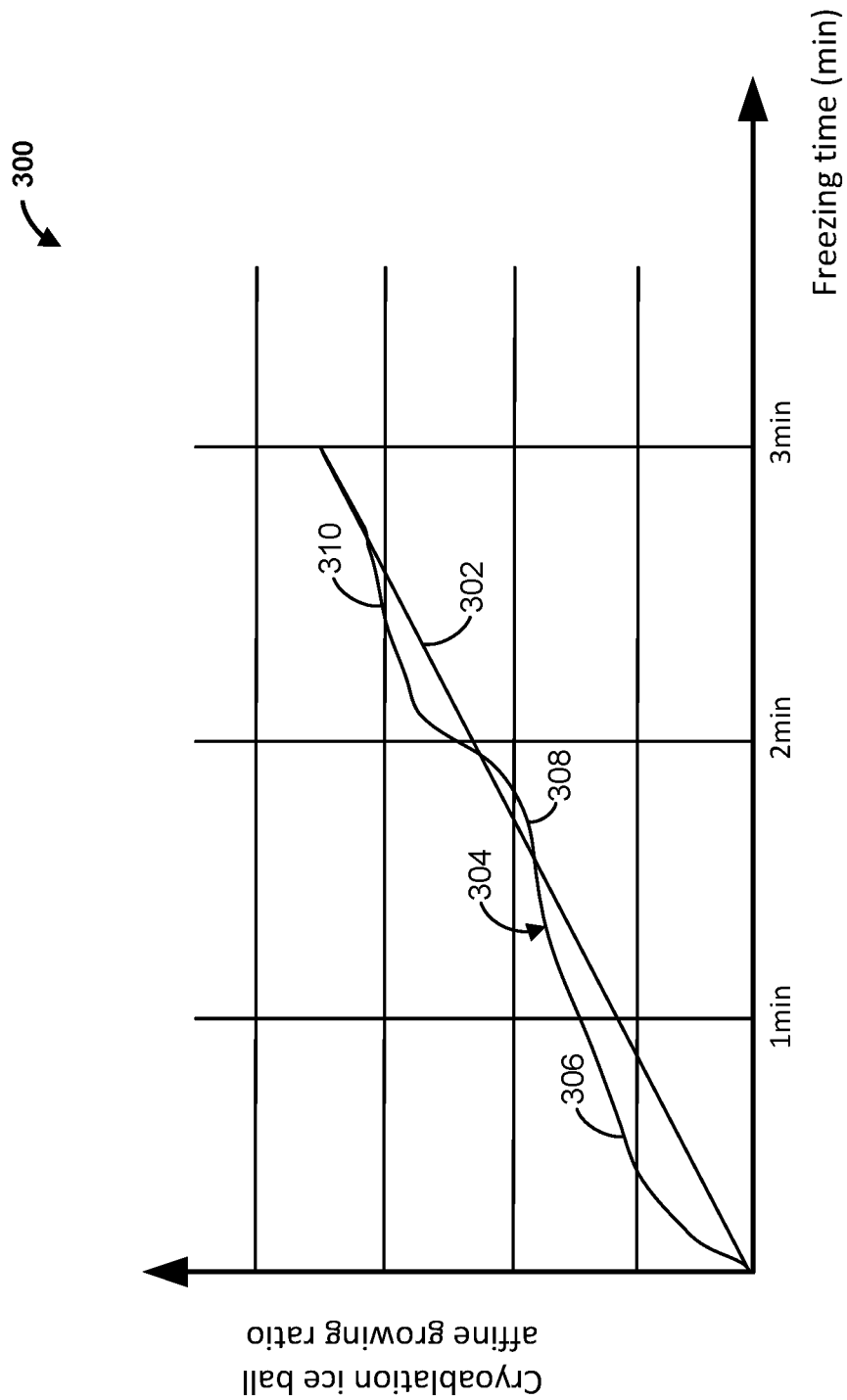
FIG. 3 is a graph illustrating an affine iceball growing ratio over time compared to a linear growing model.

One example is shown in FIG. 3. During the performance of a cryoablation treatment each of the ratios (Equations 1 to 5). The ratios can be calculated at time intervals and then compared to a predetermined target profile for each ratio. If the calculated ratio varies from the target profile by an amount greater than a predetermined threshold, the operating parameters of the cryoablation system can be adjusted or modified in the attempt to bring the ratio back to a level that more closely follows the target profile. As shown in FIG. 3, the graph 300 shows the iceball size growing affine ratio (Eq. 1) plotted as a function of time during a freezing cycle of a cryoablation treatment. The target profile for the ratio is shown as target line 302 and the calculated ratio is shown as line 304. At time 306, the calculated ratio is greater than the target line 302. In such an instance, the iceball may be growing too quickly and the pressure, flow or other operating characteristic of the cryogen may be adjusted to reduce the growth of the ice. At time 308, the calculated ratio is less than the profile line 302. The deviation is relatively small and no action may be taken unless the deviation increases to exceed a predetermined threshold. At time 310, the calculated ratio is again greater than the profile line 302. Action may be taken to reduce the growth of ice as previously described.

As can be appreciated, such an analysis can be performed by the cryoablation computing device 102 during a cryoablation treatment. While the example shown shows use of the iceball size growing affine ratio, any of the ratios previously described (i.e., Equations 1 to 5) can be used to determine whether adjustment or other action is required during a cryoablation treatment.

Figure 4:
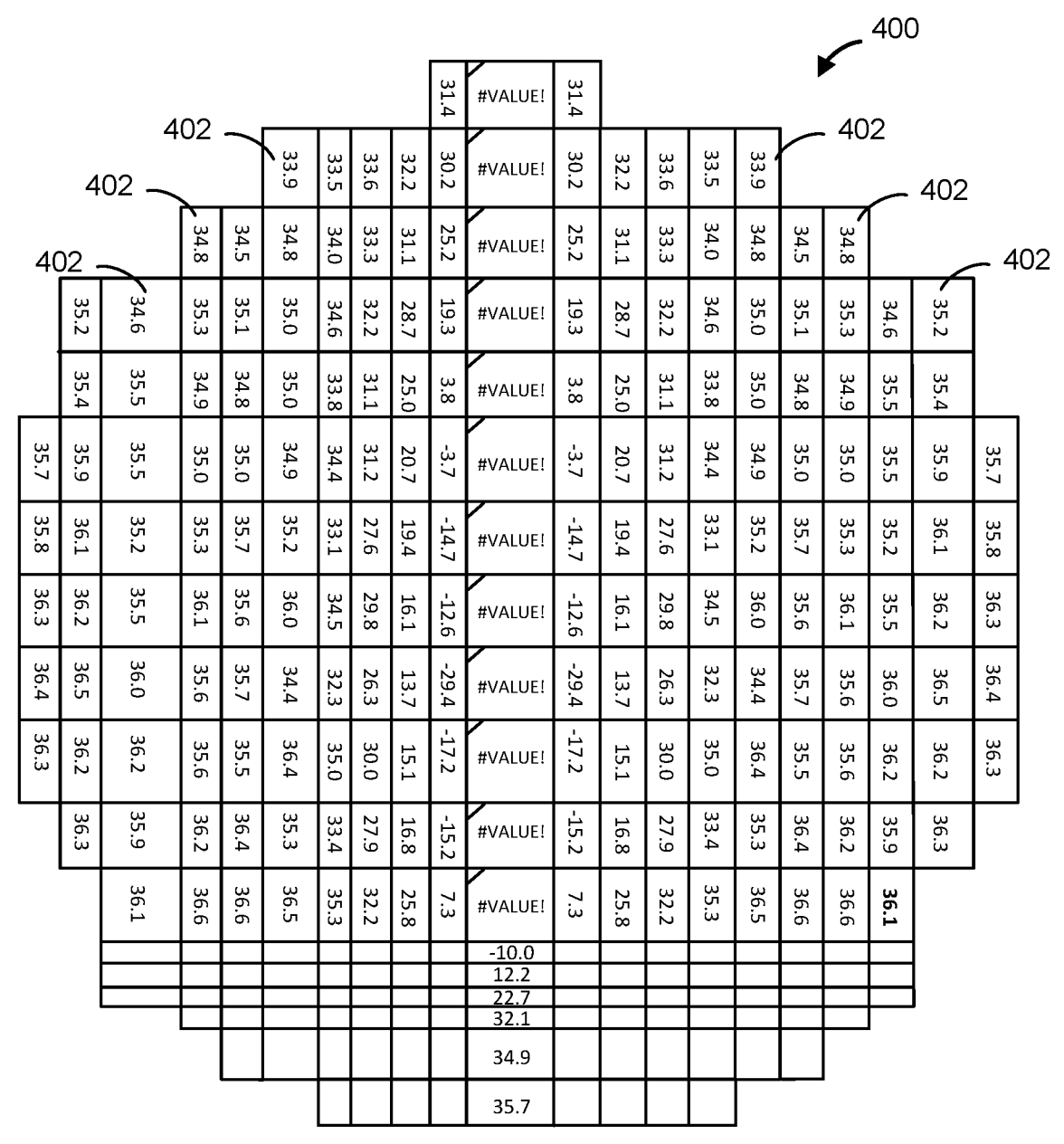
Figure 5:
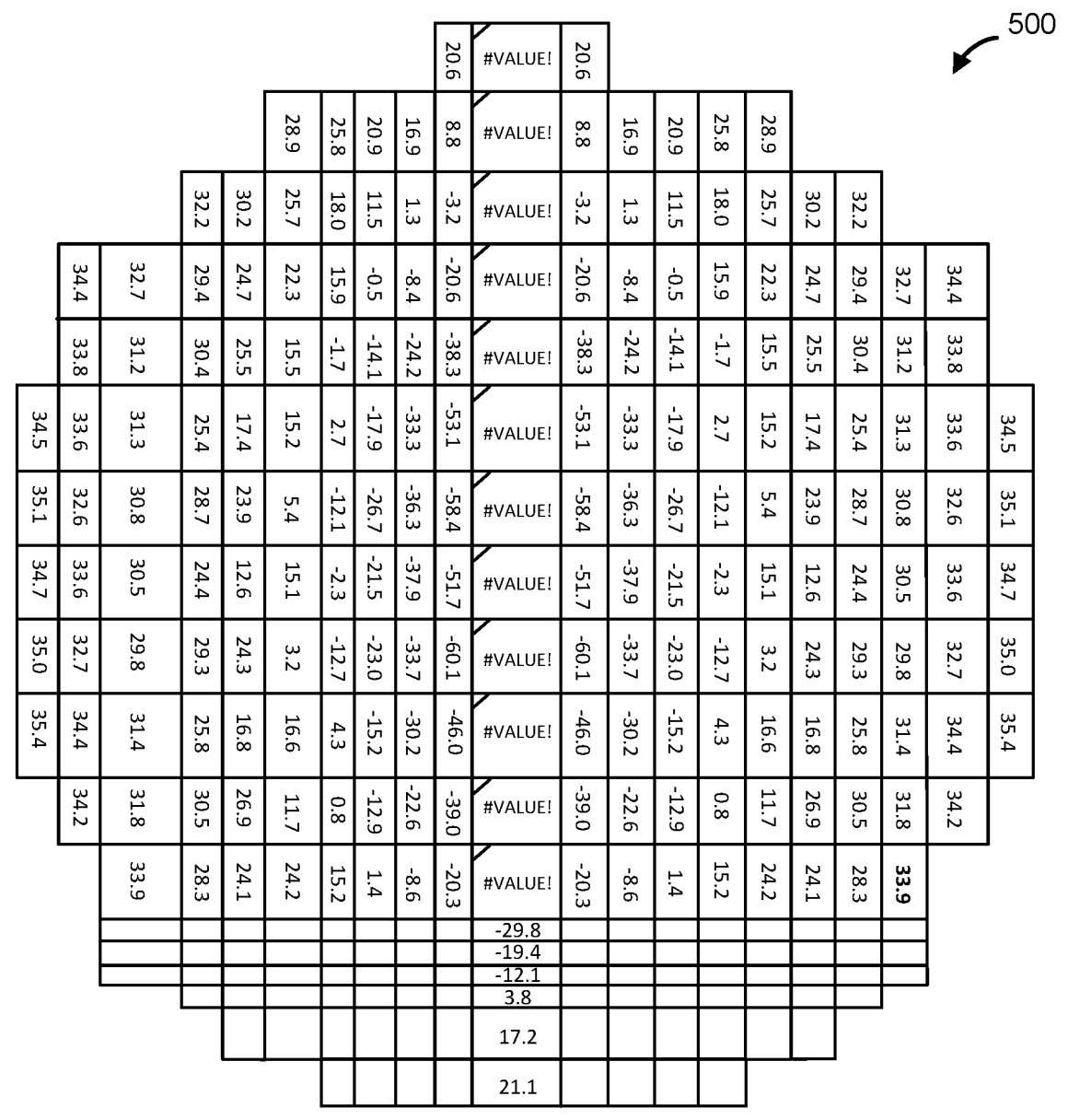

Referring now to FIGS. 4 and 5, one example method of constructing an ice formation model is shown. Experimental or clinical data of the formation of ice can be collected. The iceball can be presented using cells or finite elements shown as elements 402 in FIG. 4. The elements 402 can be used to represent a portion of the ice ball that is forming during a freezing cycle. For example, representation 400 (FIG. 4) can represent the iceball that is formed at a first time T1 of a freezing cycle. Representation 500 can represent the same iceball after it has continued to form during the same freezing cycle but shows the iceball at a second time T2 that is later in time than T1. While FIGS. 4 and 5 show the ice ball in two dimensions, the elements 402 can be made to be three dimensional cubes or rectangular prisms to construct a three dimensional representation of the iceball as well.

The representations 400 and 500 represent a size of the iceball during the corresponding time (e.g., T1 or T2). The elements 402 may include an indication of a temperature of the corresponding portion of the iceball. The temperature of the elements 402 is indicated in text and via a color or shading of the element. Using this method, representations can be created for the iceball during the time period for which data is collected or available. The algorithms, correlations, regressions or mathematical models that are created along the various directions in the affine illustration previously described can be used in conjunction with the elements 402 and/or the representations 400, 500 to determine a size, temperature, shape and location of various isotherms, such as the first isotherm 202, the second isotherm 204, and the third isotherm 206.

During the construction of the ice formation models, it can be desirable to understand non-linear and/or other complexities that contribute to or influence the growth of ice during a cryoablation treatment. In some circumstances or during some treatments, the target tissue may be located near other tissues and/or near other body structures. Neighboring or adjacent structures may act as heat sinks or otherwise influence the formation of ice during a freezing cycle. The environment of the tissue during freezing may achieve balance points or other non-linear events that may influence the formation of ice. It is desirable to understand these circumstances and events so that the ice formation model accurately and reliably predicts the formation of ice during a cryoablation treatment.

Figure 6:
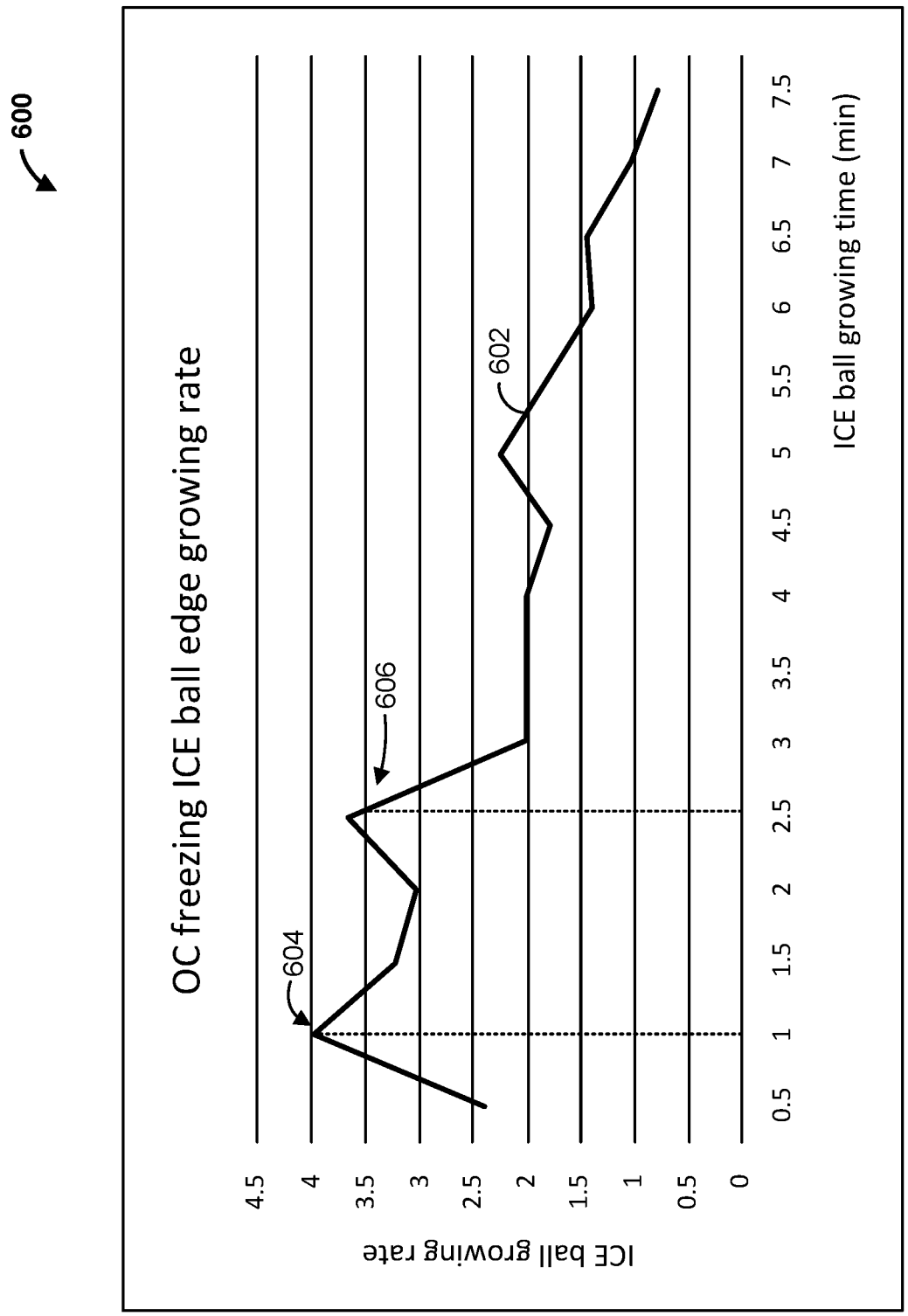
FIG. 6 is a graph illustrating an iceball growing rate over time that can be used in one or more methods of the present disclosure.

Referring now to FIG. 6, a graph 600 is shown that plots the growing rate 602 of the iceball (e.g., mm/min) versus the iceball growing time during a freezing cycle. As shown in this example, the growing rate exhibits at least two singularity points at which the growing rate rapidly increases rather than following a substantially linear path. As shown, the growing rate 602 includes a first singularity point 604 and a second singularity point 606. The first singularity point 604 occurs at about 1 minute. The second singularity point 606 occurs at about 2.5 minutes. These singularity points can be incorporated into the ice formation model so that an accurate model of ice formation can be constructed. FIG. 6 shows a plot of the growing rate of the iceball. In other examples, singularity points can be determined for other variables such as the affine ratios described above.

Figure 7:
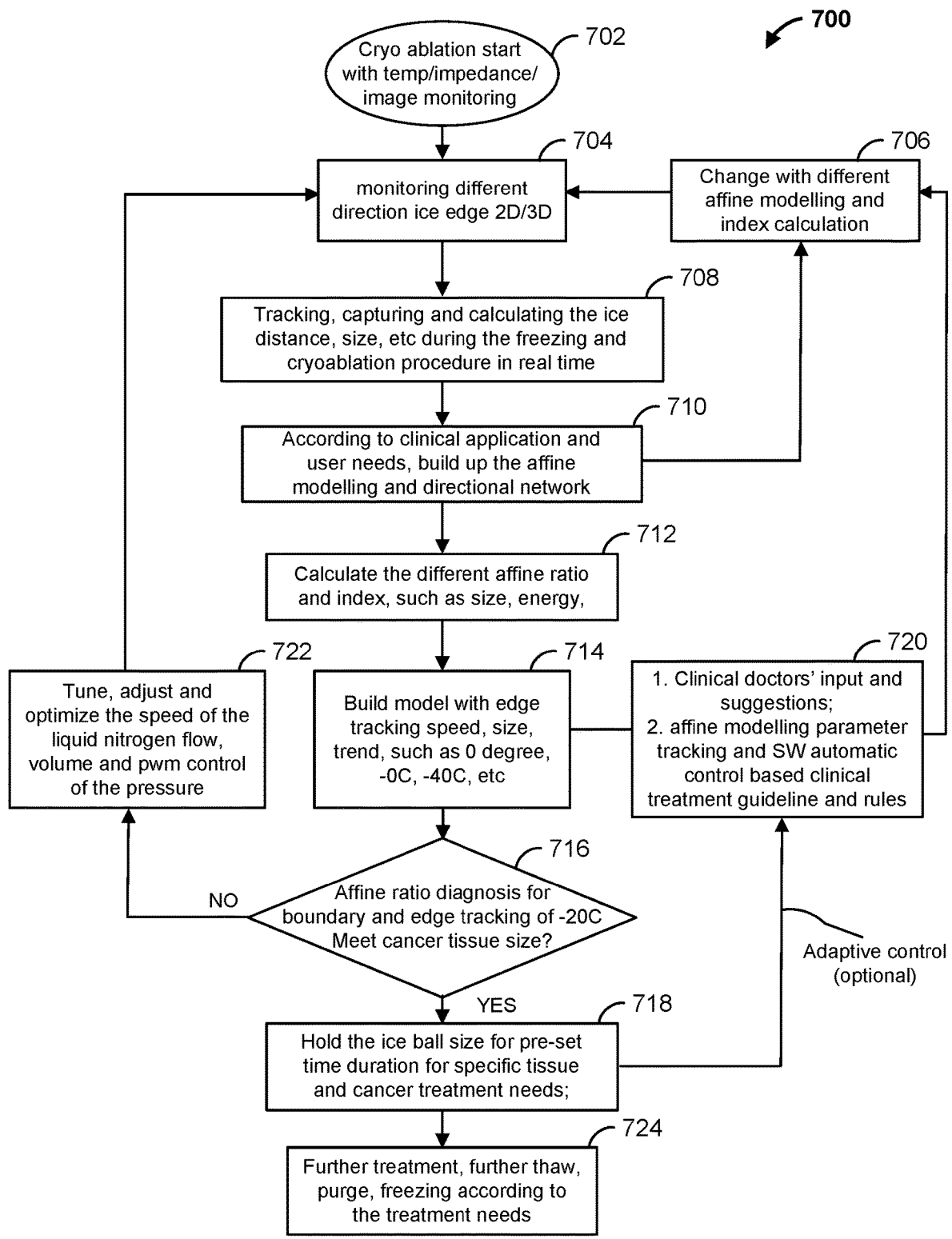
FIG. 7 is a flow chart illustrating an example method of modeling iceball growth in accordance with some embodiments of the present disclosure.

Referring now to FIG. 7, a method 700 of performing a cryoablation treatment is shown. The method 700 can be performed, for example, by the cryoablation system 100 previously described in which the steps can be performed by the cryoablation computing device 102. The method 700 can be performed by other cryoablation apparatuses and systems and/or by variations of the cryoablation system 100. For the sake of brevity, the method 700 is described with reference to the cryoablation system 100 but it should be appreciated that the method 700 is not limited to the described system and elements.

The method 700 may begin at step 702. At step 702, the freezing cycle of a cryoablation treatment may be initiated. The cryoablation computing device 102 may cause the flow of cryogen to begin flowing to the tip 122 of the cryoprobe 128. In addition, the cryoablation computing device 102 may begin monitoring ice formation data. The ice formation data may be received from imaging devices, temperature sensors, impedance sensors and the like.

The method may then move to step 704. At step 704, the cryoablation computing device 102 may monitor the ice that is being formed in the target tissue at the cryoprobe 128. Ice formation data may be obtained by the cryoablation computing device 102 from imaging devices. As previously described, the imaging data may provide information regarding the growth of the ice but typically only provides an indication of outer edge of the iceball that is growing at the target tissue. The imaging data may include two-dimensional image data or three-dimensional image data of the iceball edge that is forming at the target tissue. The imaging data may be used to determine a growth of ice in the various affine directions previously described. The growth can be determined along the eight directions or other number of directions from the predetermined location on the cryoprobe 128.

The method 700 may proceed to step 708. At step 708, the cryoablation computing device 102 may continue to track, capture, and/or calculate various aspects that characterize the growth of ice. The aspects may include a size, shape, growth rate or other characteristics of the iceball. The characteristics can be obtained and/or determined for multiple directions from the predetermined point on the cryoprobe 128 as previously described.

At step 710, the ice formation model may be modified, refined, or changed according to the clinical application and needs of the particular treatment. For example, the target tissue may be located in a particular location that may require a modification of the model in order to account for healthy tissues or body structures that may be located proximate to the target tissue. In other examples, the target tissue may have a particular size or shape such that the baseline ice formation model may not be well-suited. In other examples, other differences in the patient, type of tissue or the like may require refinement, modification or changes to the ice formation model. At step 710, the ice formation model may be changed as required and/or as requested by a medical professional. The medical professional may input such changes via a user interface in the cryoablation computing device 102, in some examples. In other examples, the cryoablation computing device may obtain information regarding the specifications of the cryoablation treatment and make such modification or changes to the ice formation model automatically. In some examples, the quantity, location and/or orientation of the directions of the affine model can be modified.

In some circumstances, the method may move back to step 706 and perform the operations of step 706. The method 700 may move back to step 706 when the ice formation model cannot be modified or changed in accordance with the medical professional's or the clinical application's needs. At step 706, the ice formation model can be modified, changed, or adjusted according to the data previously received and monitored. For example, one or more singularities may be observed that require the ice formation model to be refined, adjusted or changed.

The method 700 may alternatively proceed from step 710 to step 712. At step 712, the cryoablation computing device may determine and/or calculate the various affine ratios as previously described. the cryoablation computing device 102 may continue to obtain ice formation data and calculate the affine ratios using Equations 1 to 5.

At step 714, the cryoablation computing device 102 can build the ice formation model for the current treatment application. The ice formation model that is built at step 714 uses the relationships (or baseline models) that are obtained from previous clinical treatments and/or experimental test data. The cryoablation computing device 102 can prepare the model to provide a predicted growth of the iceball during the freezing cycle and predict a location of the first isotherm, the second isotherm, and the third isotherm. With the model, the location of a 0° C. boundary, the location of the −20° C. boundary, and the location of the −40° C. boundary can be predicted.

At step 716, the cryoablation computing device 102 can determine whether the built affine ice formation model meets the requirements of the cryoablation treatment. The cryoablation computing device 102 may determine, for example, whether the location of the −20° C. isotherm covers the target tissue such that the target tissue is completely subjected to the −20° C. freezing condition. In other examples, the cryoablation computing device 102 may determine if the location of the −40° C. isotherm corresponds to the target tissue. In still other examples, the cryoablation computing device 102 may determine what, if any, health tissue is subjected to the −40° C. and/or the −20° C. isotherms. This information may be displayed or otherwise indicated to a medical professional.

If the built ice formation model meets the requirements of the cryoablation treatment, the method may proceed to step 718. If the built ice formation model does not meet the requirements of the cryoablation treatment, the method 700 may proceed to step 722. At step 722, the cryoablation computing device 102 may tune, adjust, and/or optimize the operating conditions of the cryoablation system 100 to change the predicted growth of ice. In some examples, the pressure, flow, flow pulse, or volume of cryogen may be increased if the cryoablation computing device 102 determines that the predicted ice formation will grow too slowly or will not reach a desired size, shape or location during the freezing cycle duration time. In other examples, the cryoablation computing device 102 may reduce a pressure, flow, flow pulse, or volume of cryogen if the model indicates that the ice and/or a location of the isotherms will not reach a desired location or is growing too slowly. In still other examples, the cryoprobe 128 may be provided with one or more heating portions that can be actuated by the cryoablation computing device 102 to cause the ice to form in a desired shape or size.

At step 718, the cryoablation computing device 102 may hold an iceball for a predetermined size and duration. The size and duration of the iceball may be determined depending on the clinical needs of the treatment. For example, based on built ice formation model, the location of the iceball edge, the −20° C. isotherm, and/or the −40° C. isotherm is known. The cryoablation computing device 102 can operate the cryoablation system 100 to grow the iceball to the predicted size, shape, and location so that the target tissue is destroyed during the treatment. In many instances, the iceball is grown and maintained at a particular size, shape, and location for a predetermined period of time such as 3 minutes, 5 minutes, 10 minutes or the like. In other treatments, other predetermined durations can be used.

After step 718, the method may optionally proceed to step 720. At step 720, a medical professional may provide further input and/or adjustment, change, or modification to the ice formation model or the to the treatment specifications. As can be appreciated, circumstances may arise in the course of treatment that may require adjustments or modifications to be made. At step 720, the medical professional may make such adjustment or changes. In other examples, the cryoablation computing device 102 may automatically make changes based on data that is obtained and monitored during the course of treatment.

The method 700 may proceed to step 724 from step 718. At step 718, the cryoablation procedure may continue according to a treatment plan. The treatment plan may include a thaw cycle and subsequent freezing cycles, for example. At step 718, such further cycles or procedures may be performed to complete the cryoablation treatment.

Figure 8:
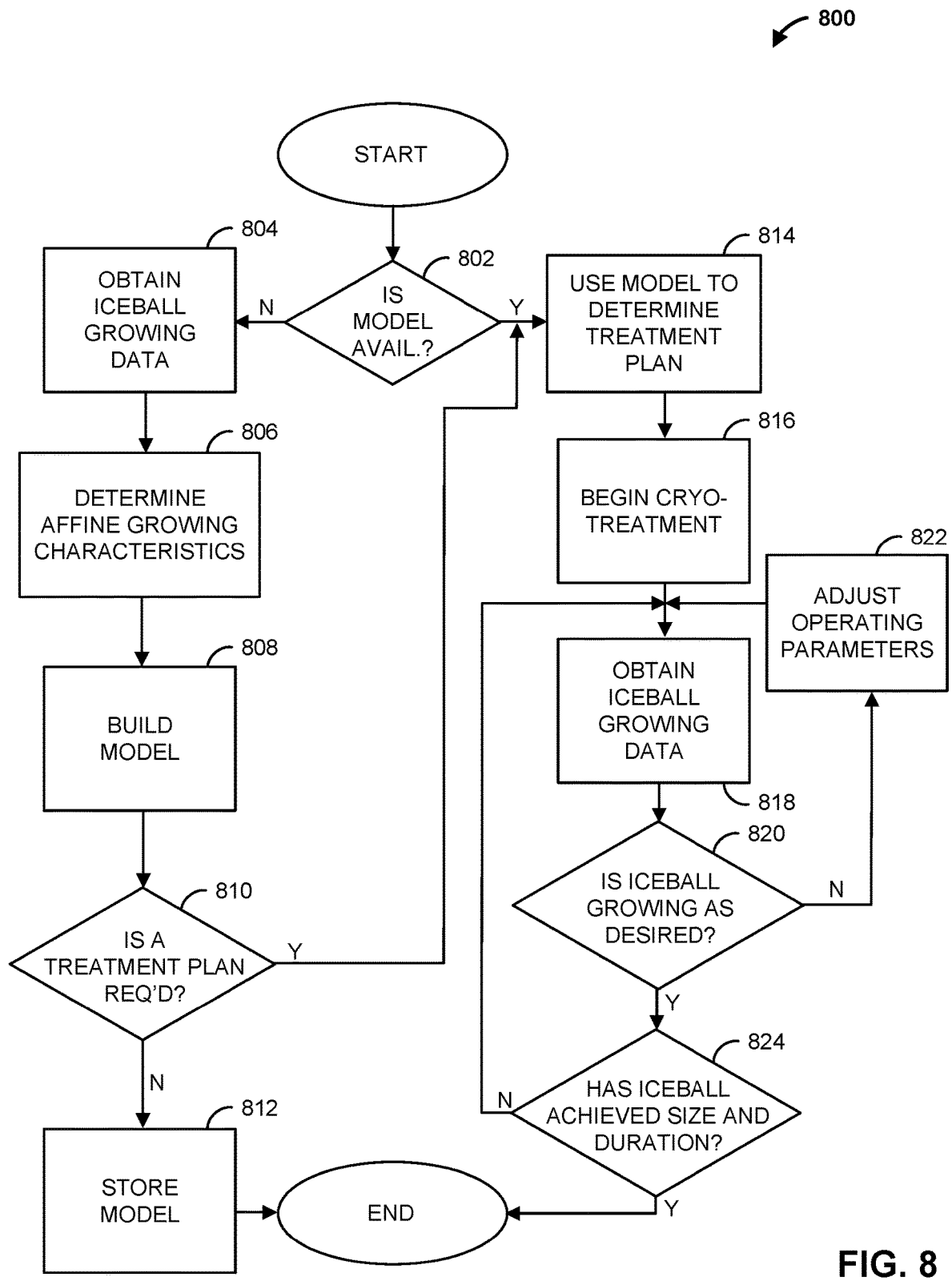
FIG. 8 is a flow chart illustrating an example method of performing a cryoablation treatment using an affine iceball growing model in accordance with some embodiments of the present disclosure.

Referring now to FIG. 8, another example method 800 of performing a cryoablation treatment is shown. The method 800, or parts thereof, may also be used to build baseline ice formation models and/or to determine the relationships between operating parameters of the cryoablation system and the growing of ice during a freezing cycle. The method 800 may be performed using various cryoablation systems. In one example, the method 800 may be performed using the cryoablation system 100. For the sake of brevity, the method 800 is described with reference to the cryoablation system 100. It should be appreciated, however, that other cryoablation systems can also be used.

The method 800 begins at step 802. At step 802, the cryoablation computing device 102 can determine whether an ice formation model is available for the current cryoablation treatment. The cryoablation computing device 102 may search or reference a clinical identification or compare the treatment details to existing ice formation models that may be stored in a suitable database or other repository. If the cryoablation computing device 102 determines that an ice formation model is available, the method proceeds to step 814. If the cryoablation computing device 102 determines that an ice formation model is not available, the method 800 proceeds to step 804.

At step 804, the cryoablation computing device 102 can obtain iceball growing data or ice formation data. The ice formation data and/or the iceball growing data may include temperature data, impedance data and/or imaging data that characterizes the growth of ice during a freezing cycle. If such data is available from historical or previous clinical treatments, such data may be used. In other examples, such data can be obtained from a test procedure or from a clinical treatment that is being performed.

At step 806, the cryoablation computing device 102 can determine and/or calculate affine growing characteristics. The affine growing characteristics may include locations of the iceball edge, a growing rate, and/or the affine ratios. These growing characteristics in connection with the operating conditions of the cryoablation system (pressure, flow, flow pulse, temperature, volume, etc.) can be analyzed to determine relationships. Regressions, correlations, machine learning models, and other suitable mathematical tools can be used to determine such relationships.

At step 808, the relationships between the growing characteristics of the iceball and the operating conditions of the cryoablation system can be used to build the ice formation model. The ice formation model can be an affine model that can predict the growth of the iceball along one or more predetermined directions from a predetermined location on the cryoprobe 128. The quantity of such directions may vary and the complexity and granularity of the model can be increased by increasing the number of affine directions at which the model is constructed or decreased by decreasing the number of affine direction at which the model is constructed. In one example, the model can be built as an affine model with eight directions oriented in each of two orthogonal planes as previously described. In other examples, the model can be constructed using more than or less than eight directions in each plane. Still further more than two orthogonal planes can also be used in other ice formation models.

At step 810, the cryoablation computing device 102 can determine whether a treatment plan is required. If a treatment plan is required, the method proceeds to step 814. If a treatment plan is not required, the method may proceed to step 812. At step 812, the cryoablation computing device 102 may store the ice formation model in a suitable database or repository for later use. As can be appreciated, the steps 804 through 812 can be used to build ice formation models. Such a process can be used in a laboratory setting, for example, to prepare baseline models that may be used during clinical treatments. Such baseline models can be used in the method 800 to begin a clinical treatment or can be used in a process such as method 700 in which the baseline model is adjusted, changed or modified according to the needs of a particular treatment.

At step 814, the ice formation model that has been built can be used to determine a treatment plan. The cryoablation computing device 102 may obtain details or other information regarding the patient, the target tissue, clinical application, standard clinical procedures and the like. The cryoablation computing device 102 may also obtain input from a medical professional via a user interface for use to create the treatment plan. In addition to including operating parameters of the cryoablation system 100, the treatment plan may also include a number of freezing or thaw cycles and the like. Once the treatment plan is finalized, the method 800 may proceed to step 816.

At step 816, the cryoablation computing device 102 may begin the cryoablation treatment. At step 816, the cryoablation computing device may initiate a flow of cryogen to the cryoprobe 128 to begin the formation of ice. While not shown, the cryoprobe 128 may be positioned at or in the target tissue. In this location, the iceball may begin to form in the target tissue. The cryoablation computing device 102 may control and/or set the operating parameters to initial conditions as may be dictated by the ice formation model and/or the treatment plan. The method 800 may then proceed to step 818.

At step 818, the cryoablation computing device 102 may obtain iceball growing data or ice formation data. The ice formation data may characterize the ice that is being formed during the freezing cycle. The ice formation data may include temperature data, impedance data and/or imaging data in some examples. The imaging data can include indications of an edge of the ice that is forming a the target tissue. The size, location and/or growing rate of the ice ball can be determined from the imaging data.

At step 820, the cryoablation computing device 102 may determine whether the iceball is growing as predicted. The cryoablation computing device 102 may compare the size, shape, location and growing rate of the iceball to the predicted iceball size, shape, location, and growing rate of the ice formation model. The ice formation model may be constructed as affine model. The comparison may be performed along the various affine directions from the predetermined location on the cryoprobe 128. The various affine ratios (Equations 1 to 5) may also be calculated and compared between the actual iceball that is forming at the target tissue and the predicted iceball of the ice formation model.

If the cryoablation computing device 102 determines that the iceball is not growing or forming as desired, the method 800 proceeds to step 822. At step 822, the cryoablation computing device 102 may change, adjust, or modify the operating parameters of the cryoablation system 100. The cryoablation computing device may adjust the pressure, flow, flow pulse, volume, temperature or other characteristic of the cryogen, for example. After step 822, the method 800 may return to step 818 and re-perform the operations as previously described.

If the cryoablation computing device 102 determines that the iceball is growing as desired, the method 800 proceeds to step 824. At step 824, the cryoablation computing device 102 determines whether the iceball has achieved a desired size and duration. The cryoablation computing device 102 can make such a determination by comparing the ice formation data to the ice formation model and/or the treatment plan. The treatment plan may include a desired duration of the freezing cycle and may include a predetermined size and location of the iceball. This may be determined so that the location of the various isotherms of the iceball are positioned relative to the target tissue so that the target tissue is destroyed during the freezing cycle. If the iceball has not achieved the desired size and duration, the method 800 returns to step 818 to re-perform operations as previously described until the iceball has achieved the desired size and duration.

If the iceball has achieved the desired size and duration, the method 800 can end. As can be appreciated, the method 800 can be re-performed for cryoablation treatments that include more than one freezing cycle.

Figure 9:
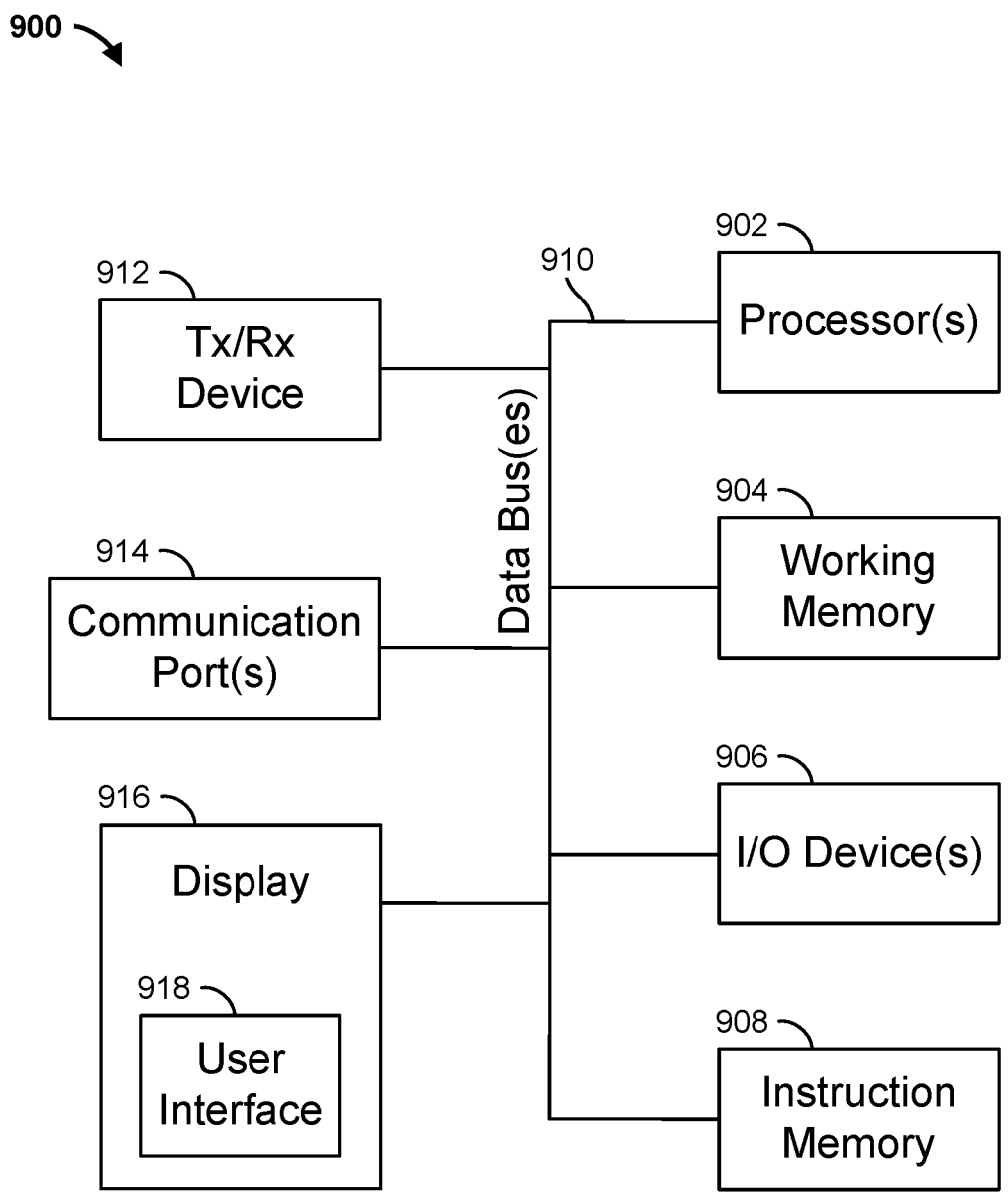
FIG. 9 is a diagram illustrating an example computing device that can be used in one or more cryoablation systems of the present disclosure.

Referring now to FIG. 9, an example computing device 900 is shown. The cryoablation system 100 may include one or more computing devices 900. For example, the cryoablation computing device 102 may have the elements shown in FIG. 9. The methods of the present disclosure, such as methods 700 and 800, may be performed, or steps of such methods may be performed, by a computing device 900.

As shown, the computing device 900 may include one or more processors 902, working memory 904, one or more input/output devices 906, instruction memory 908, a transceiver 912, one or more communication ports 914, and a display 916, all operatively coupled to one or more data buses 910. Data buses 910 allow for communication among the various devices. Data buses 910 can include wired, or wireless, communication channels.

Processors 902 can include one or more distinct processors, each having one or more cores. Each of the distinct processors can have the same or different structure. Processors 902 can include one or more central processing units (CPUs), one or more graphics processing units (GPUs), application specific integrated circuits (ASICs), digital signal processors (DSPs), and the like.

Processors 902 can be configured to perform a certain function or operation by executing code, stored on instruction memory 908, embodying the function or operation. For example, processors 902 can be configured to perform one or more of any function, step, method, or operation disclosed herein.

Instruction memory 908 can store instructions that can be accessed (e.g., read) and executed by processors 902. For example, instruction memory 908 can be a non-transitory, computer-readable storage medium such as a read-only memory (ROM), an electrically erasable programmable read-only memory (EEPROM), flash memory, a removable disk, CD-ROM, any non-volatile memory, or any other suitable memory.

Processors 902 can store data to, and read data from, working memory 904. For example, processors 902 can store a working set of instructions to working memory 904, such as instructions loaded from instruction memory 908. Processors 902 can also use working memory 904 to store dynamic data created during the operation of cryoablation computing device 102. Working memory 904 can be a random access memory (RAM) such as a static random access memory (SRAM) or dynamic random access memory (DRAM), or any other suitable memory.

Input-output devices 906 can include any suitable device that allows for data input or output. For example, input-output devices 906 can include one or more of a keyboard, a touchpad, a mouse, a stylus, a touchscreen, a physical button, a speaker, a microphone, or any other suitable input or output device.

Communication port(s) 914 can include, for example, a serial port such as a universal asynchronous receiver/transmitter (UART) connection, a Universal Serial Bus (USB) connection, or any other suitable communication port or connection. In some examples, communication port(s) 914 allows for the programming of executable instructions in instruction memory 908. In some examples, communication port(s) 914 allow for the transfer (e.g., uploading or downloading) of data, such as ice formation measurement data and the like.

Display 916 can display a user interface 918. User interfaces 918 can enable user interaction with the cryoablation computing device 102. For example, user interface 918 can be a user interface that allows an operator to interact, communicate, control and/or modify different messages, settings, or features that may be presented or otherwise displayed to a user. The user interface 918 can include a slider bar, dialogue box, or other input field that allows the user to control, communicate or modify a setting, limitation or input that is used in a cryoablation treatment. In addition, the user interface 918 can include one or more input fields or controls that allow a user to modify or control optional features or customizable aspects of the cryoablation computing device 102 and/or the operating parameters of the cryoablation system 100. In some examples, a user can interact with user interface 918 by engaging input-output devices 906. In some examples, display 916 can be a touchscreen, where user interface 918 is displayed on the touchscreen. In other examples, display 916 can be a computer display that can be interacted with using a mouse or keyboard.

Transceiver 912 allows for communication with a network. In some examples, transceiver 912 is selected based on the type of communication network cryoablation computing device 102 will be operating in. Processor(s) 902 is operable to receive data from, or send data to, a network, such as wired or wireless network that couples the elements of the cryoablation system 100.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for performing a cryoablation treatment comprising at least one computing device, the at least one computing device configured to:
   obtain an ice formation model;
   prepare a cryoablation treatment plan based on the ice formation model and one or more characteristics of the target tissue;
   initiate a cryoablation freezing cycle;
   obtain ice formation data that describes one or more characteristics of ice being formed during the cryoablation freezing cycle;
   determine a position of one or more isotherms of the ice being formed based on the ice formation data and the ice formation model;
   compare the ice formation data to the ice formation model to determine whether the ice being formed during the cryoablation treatment is growing in a predicted manner using one or more affine ratios; and
   adjust growth of the ice being formed by adjusting a flow of cryogen to a cryoprobe when the ice formation data indicates that the one or more affine ratios are greater than a predetermined upper threshold or less than a predetermined lower threshold.

2. The system of claim 1, wherein the ice formation model describes a growth of ice and a temperature as a function of time during a cryoablation freezing cycle in a plurality of linear directions multiple directions from a predetermined position on a cryoablation probe.

3. The system of claim 1, wherein the ice formation model comprises an affine model configured to predict growth of ice in a plurality of directions from a predetermined position on a cryoablation probe.

4. The system of claim 1, wherein the one or more characteristics of the target tissue comprises a type of tissue, a size of the tissue, and a shape of the tissue.

5. The system of claim 1, wherein the ice formation data comprises imaging data obtained from an imaging apparatus.

6. The system of claim 5, wherein the imaging data indicates an outer edge of the ice being formed during the cryoablation cycle.

7. The system of claim 1, wherein each isotherm of the one or more isotherms indicates a boundary at which a predetermined temperature threshold has been reached.

8. The system of claim 7, wherein at least one of the one or more isotherms corresponds to a boundary at which the ice has reached −20° C.

9. The system of claim 1, wherein the step of determining a position of one or more isotherms comprises determining a position relative to the cryoablation probe of a boundary at which ice has reached −20° C. based on a position of an edge surface of the ice and the ice formation model.

10. A method of performing a cryoablation treatment comprising:
    obtaining an ice formation model;
    preparing a cryoablation treatment plan based on the ice formation model and one or more characteristics of the target tissue;
    initiating a cryoablation freezing cycle;
    obtaining ice formation data that describes one or more characteristics of ice being formed during the cryoablation freezing cycle; and
    determining a position of one or more isotherms of the ice being formed based on the ice formation data and the ice formation model;
    compare the ice formation data to the ice formation model to determine whether the ice being formed during the cryoablation treatment is growing in a predicted manner using one or more affine ratios; and
    adjust growth of the ice being formed when the ice formation data indicates that the one or more affine ratios are greater than a predetermined upper threshold or less than a predetermined lower threshold.

11. The method of claim 10, wherein the ice formation model describes a growth of ice and a temperature as a function of time during a cryoablation freezing cycle in multiple directions from a predetermined position on a cryoablation probe.

12. The method of claim 10, wherein the ice formation model comprises an affine model configured to predict growth of ice in a plurality of directions from a predetermined position on a cryoablation probe.

13. The method of claim 10, wherein the one or more characteristics of the target tissue comprises a type of tissue, a size of the tissue, and a shape of the tissue.

14. The method of claim 10, wherein the ice formation data comprises imaging data obtained from an imaging apparatus.

15. The method of claim 14, wherein the imaging data indicates an outer edge of the ice being formed during the cryoablation cycle.

16. The method of claim 10, wherein each isotherm of the one or more isotherms indicate a boundary at which a predetermined temperature threshold has been reached.

17. The method of claim 10, wherein at least one of the one or more isotherms corresponds to a boundary at which the ice has reached −20° C.

18. The method of claim 10, wherein the step of determining a position of one or more isotherms comprises determining a position relative to the cryoablation probe of a boundary at which ice has reached −20° C. based on a position of an edge surface of the ice and the ice formation model.

19. The system of claim 1, wherein the one or more affine ratios comprises an affine growing ratio characterizing a growth of ice along one of a plurality of linear directions from a predetermined point on a cryoprobe.

20. The method of claim 10, wherein the one or more affine ratios comprises an affine growing ratio characterizing a growth of ice along one of a plurality of linear directions from a predetermined point on a cryoprobe.

* * * * *